United States Patent [19]

Takeuchi et al.

[11] Patent Number: 5,124,655
[45] Date of Patent: Jun. 23, 1992

[54] SENSOR SYSTEM FOR DETECTING MIXING RATIO OF MIXED FUEL

[75] Inventors: Kiyoshi Takeuchi, Kanagawa; Kazumitsu Kobayashi, Gunma, both of Japan

[73] Assignees: Nissan Motor Company, Limited; Japan Electronics Control Systems Co., Ltd., both of Japan

[21] Appl. No.: 617,073

[22] Filed: Nov. 23, 1990

[30] Foreign Application Priority Data

Nov. 25, 1989 [JP] Japan .................................. 1-305734

[51] Int. Cl.⁵ .......................................... G01N 27/22
[52] U.S. Cl. .................................. 324/690; 324/686; 324/663

[58] Field of Search ............... 324/663, 686, 689, 690, 324/446, 448, 450; 73/61.1 R

[56] References Cited

U.S. PATENT DOCUMENTS

4,939,468  7/1990  Takeuchi ............................. 324/690

Primary Examiner—Jack B. Harvey
Attorney, Agent, or Firm—Lowe, Price, LeBlanc & Becker

[57] ABSTRACT

A fuel mix ratio sensor system comprises a cylindrical housing having a small diameter portion on one end at which an electrode is supported. A sealing means, such as an O-ring, directly contacts an inner periphery of the small diameter portion in order to secure the sensor against leakage of the detected fluid.

21 Claims, 6 Drawing Sheets

SENSOR SYSTEM FOR DETECTING MIXING RATIO OF MIXED FUEL

BACKGROUND OF THE INVENTION

1. Field of the Invention

The present invention relates generally to a sensor system for detecting a mix ratio of a fluid mixture passing through a cylindrical pipe. More specifically, the invention relates to a sensor system for detecting mixing ratio of mixture of petroleum fuel and alcohol which is to be introduced into an engine.

2. Description of the Background Art

In recent years, mixtures of petroleum fuel and alcohol have been used as fuel for driving engines and so forth in order to decrease dependency upon petroleum. In a case where such a mixed fuel is used, it is required that the mixing ratio of petroleum fuel to alcohol is detected for controlling a fuel injection amount and a spark ignition timing on the basis of the detected mixing ratio so as to always obtain optimum output if the mixing ratio varies.

Figure 1:
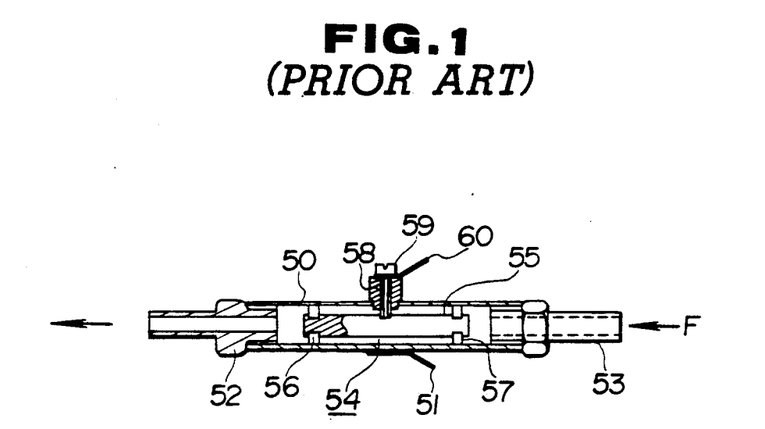
FIG. 1 is a sectional view of a conventional sensor system.

One conventional sensor system for detecting the mixing ratio of the mixture of petroleum fuel and alcohol is shown in FIG. 1. This sensor system has a cylindrical container 50 made of metal, which is connected to an earth cable 51 to serve as an external electrode. Connectors 52 and 53 are mounted on both end portions of the cylindrical container 50 to define therein a fuel passage 54. An internal electrode 55 is arranged within the fuel passage 54 so that both end portions thereof are supported on support members 56 and 57 made of an insulating material. A bolt 59 is inserted into a through opening formed in the cylindrical container 50 via a bush 58. The bolt 59 is formed with a screw portion at the end thereof, and the screw portion engages the internal electrode 55. In addition, the bolt 59 is connected to a lead 60.

Figure 2:
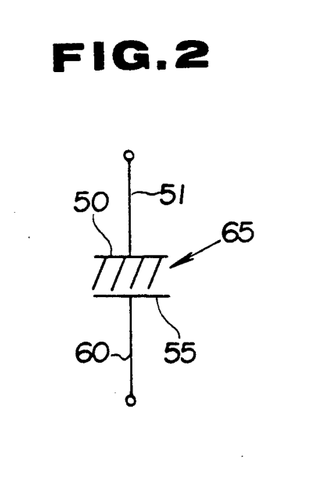
FIG. 2 is a schematic view of a circuit equivalent to an electrical capacitance type sensor.

After fuel hoses are connected to the connectors 52 and 53, when the fuel F, which is a mixture of petroleum fuel and alcohol, passes through the cylindrical container 50, a condenser 65 is formed in which the fuel F serves as a dielectric material between the cylindrical container (external electrode) 50 and the internal electrode 55 as shown by an equivalent circuit of FIG. 2.

Generally, electrostatic capacity C [the fuel F] of the condenser 65 can be expressed by the following formula.

$$C = \frac{A}{t} \times \frac{\epsilon}{\epsilon_0} \times \epsilon_0$$

A: Area of Electrode [cm$^2$]
t: Distance between Electrodes [cm]
$\epsilon$: Dielectric Constant of Dielectric Material [F/cm]
$\epsilon_0$: Dielectric Constant in Vacuum ($=8,854\times10^{-4}$) [F/cm]
$\epsilon/\epsilon_0$: Dielectric Constant of Dielectric Material Therefore, if A and t are constant, electrostatic capacity C [F] varies in proportion to the dielectric constant $\epsilon/\epsilon_0$ of dielectric material, so the dielectric constant of dielectric material, i.e. fuel F, can be obtained by detecting electrostatic capacity C [F]. For example, dielectric constants of gasoline and methanol are about 1.95 and 32.4, respectively. Since dielectric constant of a mixed fuel varies in accordance with its mixing ratio, the mixing ratio of the mixed fuel F can be obtained by detecting its electrostatic capacity C [F].

Figure 4:
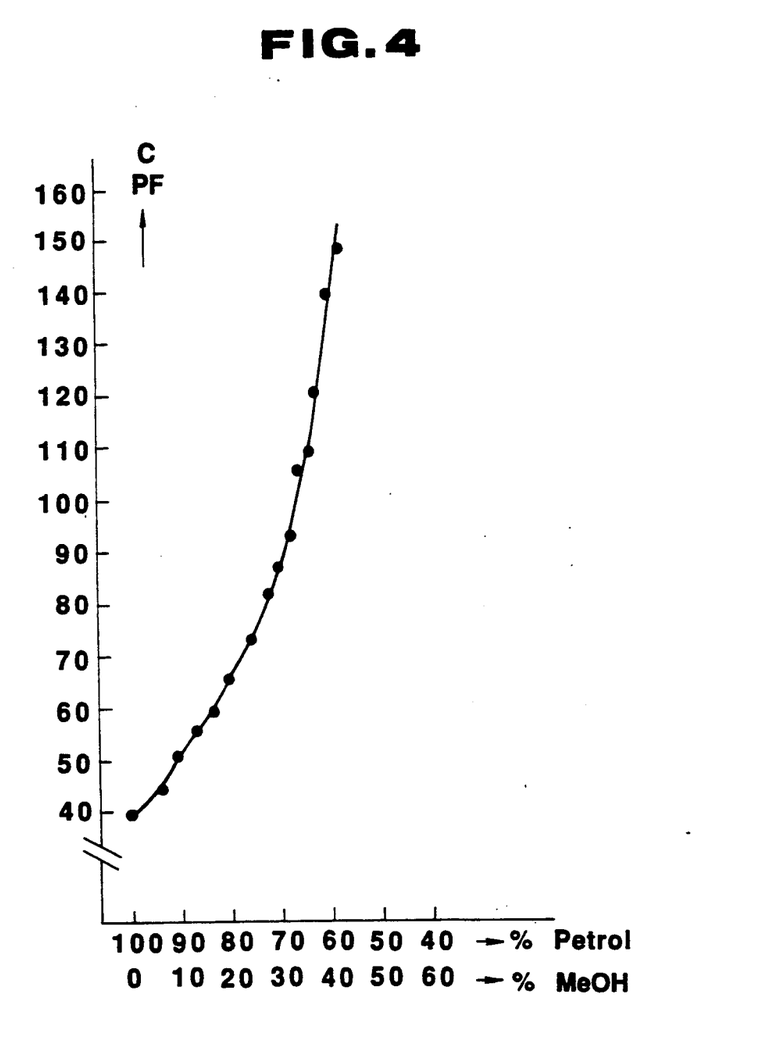
FIG. 4 is a circuit diagram of a detecting circuit.

FIG. 4 is an example of variation of electrostatic capacity C relative to mixing ratio of a mixture of petroleum fuel and methanol. From this graph, it is understood that the mixing ratio of the mixed fuel F can be obtained by detecting electrostatic capacity C.

Figure 3:
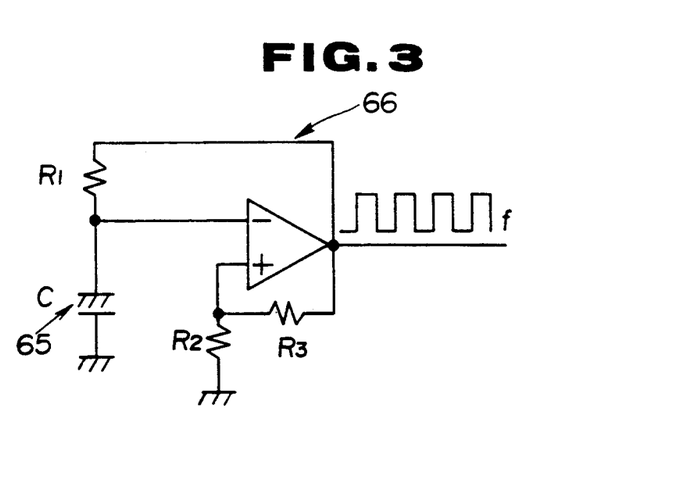
FIG. 3 is a graph showing a relationship between a mixing ratio of mixed fuel and electrostatic capacity.

This electrostatic capacity C is input to, e.g. an oscillating circuit 66 as shown in FIG. 3. This oscillating circuit 66 outputs an oscillating frequency f determined on the basis of circuit constants, such as resistances $R_1$, $R_2$ and $R_3$, and of electrostatic capacity C, so that variation of the electrostatic capacity, and thereby variation of the mixing ratio, is detected via variation of oscillating frequency f.

However, in such conventional sensor systems, since the electrical connecting portion is closed from the outside of the cylindrical container only by means of the bolt 59, the bolt 59 tends to be pushed out to cause leakage of fuel when fuel pressure increases.

Figures 5A, 5B:
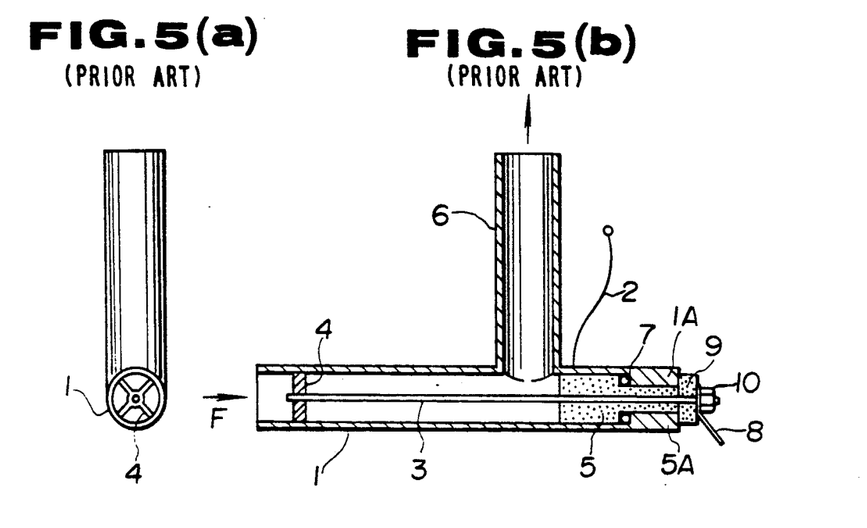
FIGS. 5(a) and 5(b) are sectional and perspective views of a modified sensor system.

In order to eliminate the aforementioned disadvantage, the inventors of the present invention have previously disclosed an improved fluid detecting sensor system as shown in FIGS. 5(a) and 5(b) in Japanese Patent First (unexamined) Publication (Tokkai Hei.) No. 1-196557. In this sensor system, a cylindrical container 1 made of metal is connected to a lead 2 to serve as an external electrode. The cylindrical container 1 has an open end which serves as an inlet port for introducing fuel F into the cylindrical container 1 and which also serves as a connector. An internal electrode 3 is arranged within the cylindrical container 1. The supply-side end portion of the internal electrode 3 is supported on a support member 4 which is similar to that of conventional sensor systems. If the internal electrode 3 has relatively high rigidity, the support member 4 is not required. The other end portion of the internal electrode 3 is supported on a plug-type support member 5 by which one end of the cylindrical container 1 is closed. In addition, the cylindrical container 1 is in fluid communication with a fuel discharge pipe 6 which projects at a location upstream of the plug-type support member 5 in an essentially radial direction of the cylindrical container 1 and which also serves as a connector.

Connection between the cylindrical container 1 and the fuel discharge piper 6 is performed by, for example, brazing. After rust, stains, and so forth are removed from the inner and outer surfaces, nickeling and so forth are performed.

The plug-type support member 5 has a small-diameter portion 5A on the opposite side to the supply side within the cylindrical container 1. The cylindrical container 1 is formed with a small-diameter supporting portion 1A for receiving therein the small-diameter portion 5A of the plug-type support member 5. An O-ring 7 is arranged between the facing surfaces of the small-diameter portion 1A and the support member 5. In addition, the internal electrode 3 passes through the plug-type support member 5 to project from the cylindrical container 1 to be secured to the end portion of the cylindrical container 1 by means of a nut 10 via a insulating bush 9 made of Teflon or the like which has a small dielectric constant and a small dielectric loss. The projecting end portion of the internal electrode 3 is connected to an output terminal 8.

After fuel hoses are connected to the cylindrical container 1 and the fuel discharge pipe 6, the mixed fuel is introduced into the cylindrical container 1 to be discharged from the fuel discharge pipe 6, so that the mixing ratio of the mixture of gasoline and alcohol can be measured in a manner similar to the aforementioned manner. Generally, pressure of this mixed fuel increases to about 10 kg/cm² to thrust the plug-type support member 5 toward the small-diameter portion 1A. This thrusting force is received by the small-diameter portion 1A via the O-ring 7, so that the O-ring 7 deforms to improve sealing performance between the support member 5 and the cylindrical container 1 so as to prevent leakage of fuel F.

However, in this type of sensor system, manufacturing accuracy of the contact surface of the cylindrical container 1, which comes into contact with the O-ring 7, becomes difficult due to thermal distortion when brazing, so that sealing performance of the O-ring 7 becomes insufficient. That is, since the contact surface, particularly the inner peripheral surface, of the cylindrical container 1 is formed by inserting a tool, such as a drill, into the cylindrical container 1 from the left in FIG. 5(b), manufacturing accuracy of the contact surface of the cylindrical container 1 can not be optimally formed when the cylindrical container 1 distorts due to brazing of the fuel discharge pipe 6 to the cylindrical container 1.

SUMMARY OF THE INVENTION

It is therefore a principal object of the present invention to provide an improved sensor system which can fully interrupt leakage of a detected fluid introduced into a cylindrical container.

It is another object of the present invention to provide an improved sensor system with a sealing surface to fully prevent leakage of the detected fluid and which can be easily manufactured.

In order to accomplish the aforementioned and other objects, a cylindrical container of a sensor system is formed with an annular projecting portion, the inner periphery of which comes into contact with a sealing member to interrupt leakage of a detected fluid.

According to one aspect of the present invention, a sensor system for detecting a physical quantity of fluid, comprises: an essentially cylindrical container serving as an external electrode and defining therein an internal space through which a detected fluid passes, the cylindrical container having first and second open end portions, the first open end portion serving as an inlet port for introducing the detected fluid into the interior thereof, the second open end portion being formed with an annular projecting portion which projects inwardly from the inner periphery of the cylindrical container and which extends in a circumferential direction of the cylindrical container; an internal electrode housed within the cylindrical container; a supporting member received within the cylindrical container to close the second open end portion at a location upstream of the annular projecting portion, and supporting a portion of the internal electrode thereon to hold the internal electrode at a predetermined position within the cylindrical container; a discharge passage communicated with the cylindrical container and having an open end which serves as a discharge port for discharging the detected fluid to the outside; and sealing means tightly coming into contact with the inner periphery of the annular projecting portion of the cylindrical container to interrupt leakage of the detected fluid between the outer periphery of the supporting means and the inner periphery of the cylindrical container.

BRIEF DESCRIPTION OF THE DRAWINGS

The present invention will be understood more fully from the detailed description given herebelow and from the accompanying drawings of the preferred embodiments of the invention. However, the drawings are not intended to imply limitation of the invention to a specific embodiment, but are for explanation and understanding only.

In the drawings.

DESCRIPTION OF THE PREFERRED EMBODIMENT

Figure 6:
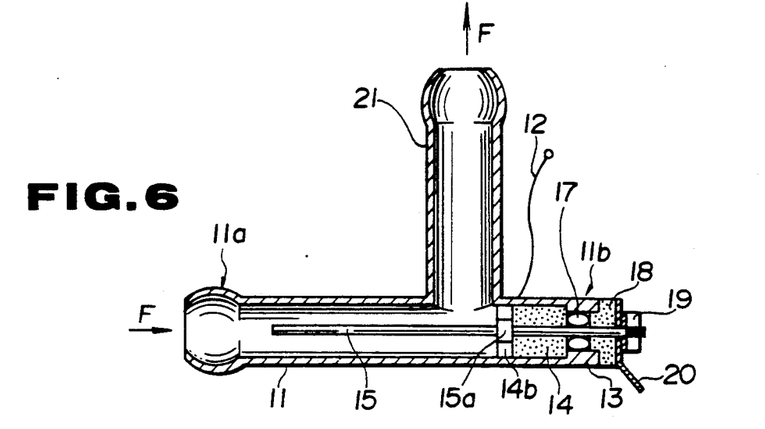
FIG. 6 is a sectional view of the first preferred embodiment of a sensor system according to the present invention.
Figure 7:
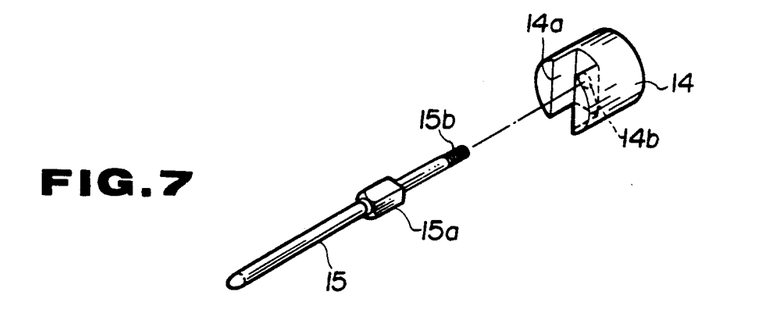
FIG. 7 is a perspective view of an internal electrode of the sensor system of FIG. 6.

Referring now to the drawings, particularly to FIGS. 6 and 7, the first preferred embodiment of a sensor system, according to the present invention.

The sensor system has a cylindrical container 11 made of a metal. The cylindrical container 11 is connected to a lead line 12 which serves as an external electrode. The cylindrical container 11 has an open end 11a through which fuel F is supplied to the interior of the cylindrical container 11. The open end 11a expands radially to serve as a connecting portion. The cylindrical container 11 also has a closed end 11b at the opposite end to the open end 11a. The closed end 11b is formed with a small-diameter portion 13. A plug-type support member 14 is inserted into the cylindrical container 11 from the open end 11a to be secured to the inner side wall of the small-diameter portion 13. The plug-type support member 14 is made of an insulator, such as Teflon (polytetrafluorethylene).

The cylindrical container 11 houses therein an internal electrode 15 which extends in a longitudinal direction of the cylindrical container 11. One end portion of the internal electrode 15 passes through the plug-type support member 14 to be supported thereon. As shown in FIG. 7, the internal electrode 15 has an essentially cylinder shape. The internal electrode 15 has a square pillar portion 15a at the central portion thereof, and a screw portion 15b at one end portion thereof. The square pillar portion 15a engages a groove 14a formed in the plug-type support member 14 to be fixed thereto by using a tool or the like, so that the internal electrode 15 can be prevented from rotating relative to the plug-type support member 14. Furthermore, the plug-type support member 14 has a cylindrical bore 14b through which the internal electrode 15 passes.

An O-ring 17 is arranged within the cylindrical container 11 so that the outer periphery of the O-ring 17 is in tight contact with the inner surface of the small-diameter portion 13. The O-ring 17 receives therethrough the internal electrode 15 so that the inner surface of the O-ring 17 is in tight contact with the outer periphery of the internal electrode 15. In this way, the O-ring 17 prevents leakage of fuel between the outer periphery of the internal electrode 15 and the inner periphery of the plug-type support member 14 and between the outer periphery of the plug-type support member 14 and the inner periphery of the cylindrical container 11.

In addition, an insulator bush member 18 is set in the small-diameter portion 13 to thrust the O-ring 17 against the plug-type support member 14. The screw portion 15b of internal electrode 15, which passes through the insulator bush member 18 to project therefrom, engages a nut 19. By tightening the nut 19, an output terminal 20 is fixed to the insulator bush member 18, and the square pillar portion 15a urges the plug-type support member 14 to the inner side wall of the small-diameter portion 13. Furthermore, a fuel discharge pipe 21 projects at a location upstream of the plug-type support member 14 in an essentially radial direction of the cylindrical container 11 to establish a fluid communication with the cylindrical container 11. The fuel discharge pipe 21 has an open end which expands radially to serve as a connecting portion.

With this construction, fuel hoses are connected to the open end 11a of the cylindrical container 11 and the open end of the fuel discharge pipe 21, for allowing mixed fuel to enter the cylindrical container 11 to exit the fuel discharge pipe 21, so that mixing ratio of a gasoline/alcohol mixture can be measured in a known manner. Generally, the mixed fuel pressure increases to about 10 kg/cm$^2$. This pressure urges the plug-type support member 14 to the inner side wall of the small-diameter portion 13. For that reason, as the fuel pressure increases, pressure for thrusting the plug-type support member 14 to the inner side wall of the small-diameter portion 13 increases to enhance sealing of fuel between the plug-type support member 14 and the inner side wall of the small-diameter portion 13. In addition, the O-ring 17 interrupts fuel leakages between the outer periphery of the internal electrode 15 and the inner periphery of the plug-type support member 14 and between the outer periphery of the plug-type support member 14 and the inner periphery of the cylindrical container 11, to prevent fuel from leaking.

In this case, since wall thickness of the small-diameter portion 13 which comes into contact with the O-ring 17 is sufficiently thick, deformation of the small-diameter portion 13 due to brazing of the fuel discharge pipe 21 to the cylindrical container 11 is relatively small. Therefore, the inner surface of the small-diameter portion 13 can be finished at a desired accuracy, so that leakage of fuel due to low accuracy of contact surface in conventional sensor systems can be prevented. In addition, by chamfering the inner edge portion of the small-diameter portion 13, the O-ring 17 can be easily inserted into the small-diameter portion 13.

Figure 8:
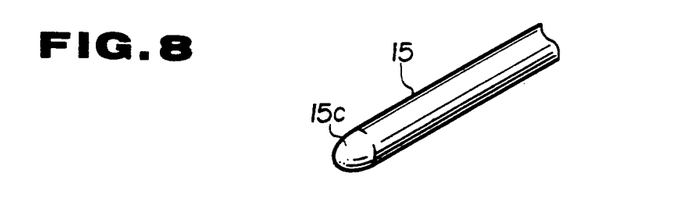
FIG. 8 is a perspective view of an end portion of the internal electrode of FIG. 7.

As shown in FIG. 8, when the tip 15c of the internal electrode 15 on the side of the open end of the cylindrical container 11 is cut round, it is possible to prevent agitation of the mixed fuel passing through the cylindrical container 11 thereby decreasing occurrence of bubbles in the mixed fuel. As a result, it is possible to prevent the dielectric constant from decreasing due to occurrence of bubbles so that the measuring accuracy can be improved.

Figure 9:
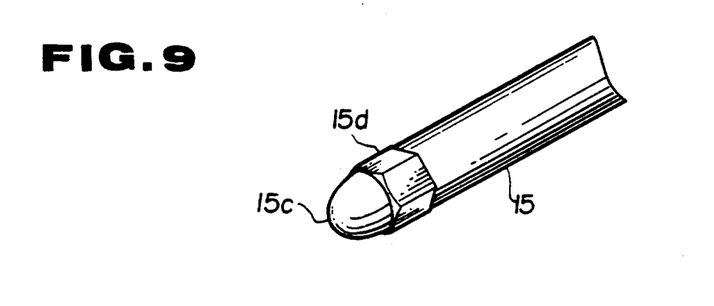
FIG. 9 is a perspective view of a modified end portion of the internal electrode of FIG. 7.

Furthermore, as shown in FIG. 9, the end portion of the internal electrode 15 may be formed with a hexagonal portion 15d which can be used for applying a whirl-stop to the internal electrode 15 when fastening the nut.

Figure 10:
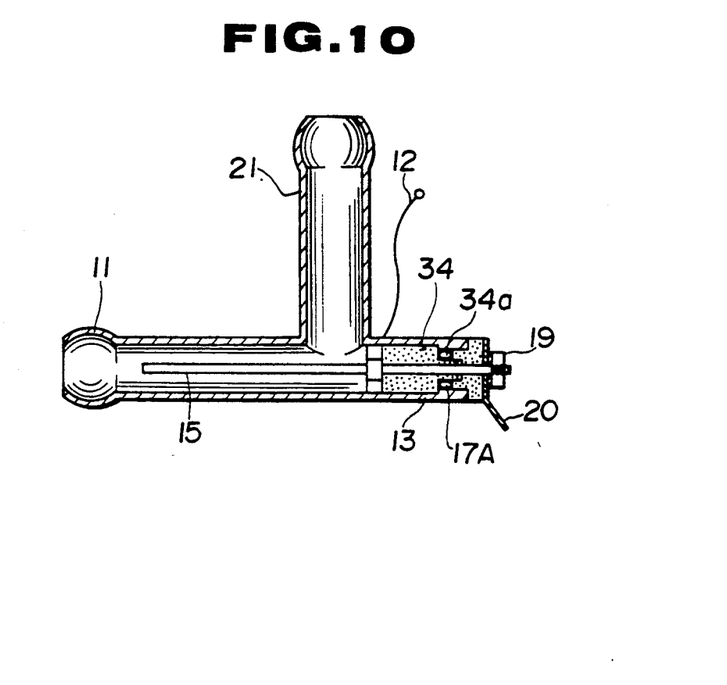
FIGS. 10 to 12 are sectional views of second, third and fourth preferred embodiments of a sensor system according to the present invention, respectively.

FIG. 10 shows the second preferred embodiment of a sensor system, according to the present invention. In this embodiment, a plug-type support member 34 is substituted for the plug-type support member 14 of the aforementioned preferred embodiment. The plug-type support member 34 is formed with a projecting portion 34a which projects towards the closed end portion of the cylindrical container 11. An O-ring 17A is arranged between the left-facing periphery of the projecting portion 34a and the inner periphery of the small-diameter portion of the cylindrical container 11 to interrupt leakage of fuel between the outer periphery of the plug-type support member 34 and the inner periphery of the cylindrical container 11. In addition, the internal electrode 15 passes through the plug-type support member 34 so as to interrupt leakage of fuel between the outer periphery of the internal electrode 15 and the inner periphery of the plug-type support member 34.

As mentioned above, since electrostatic capacity produced between the internal electrode 15 and the cylindrical container 11 is input to the oscillating circuit as shown in FIG. 3, it is required that a low electrical loss material is selected as the insulating material, to be arranged between the internal electrode 15 and the cylindrical container 11, in order to stabilize oscillation of the oscillating circuit.

However, in a case where the O-ring 17 made of, e.g. fluororubber, is arranged between the internal electrode 15 and the cylindrical container 11 as shown in FIG. 6, the dielectric constant and dielectric loss become great, which is undesirable. For example, the dielectric constant of fluororubber is greater than 6, and dielectric loss thereof is greater than 3%. Therefore fluororubber is not preferable for the first embodiment. However, in the case of the construction of FIG. 10, an O-ring made of fluororubber having high dielectric constant and dielectric loss may be used, as the O-ring does not directly contact the electrode 15. The high rigidity of fluororubber insures a tight seal between the outer surface of the electrode 15 and the inner periphery of the supporting member 34.

Figure 11:
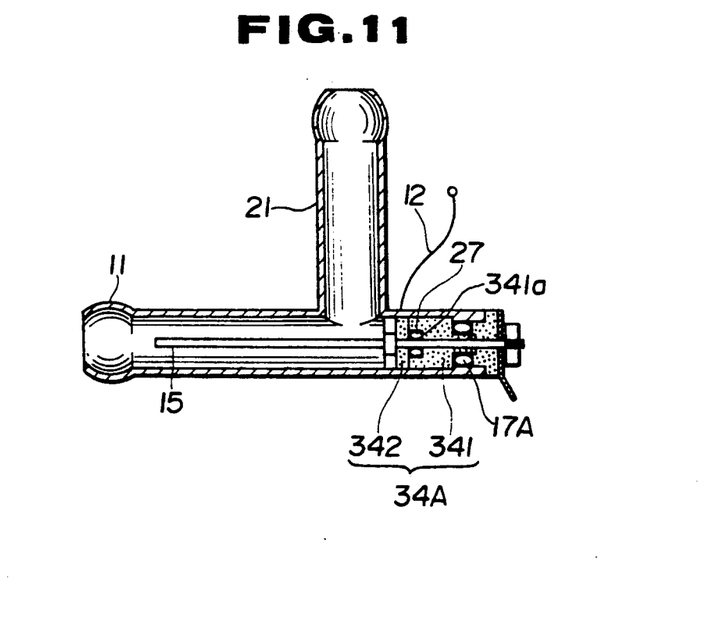

FIG. 11 shows the third preferred embodiment of a sensor system, according to the present invention. In this embodiment, a plug-type support assembly 34A is substituted for the plug-type support member 34 of the second preferred embodiment. The plug-type support assembly 34A comprises two support members 341 and 342. One support member 341 has a recessed portion 341a at its left-facing end surface. An O-ring 27 through which the internal electrode 15 is inserted, is arranged within the recessed portion 341a, so as to establish sealing between the outer periphery of the internal electrode 15 and the support assembly 34A, providing a very high degree of sealing.

Figure 12:
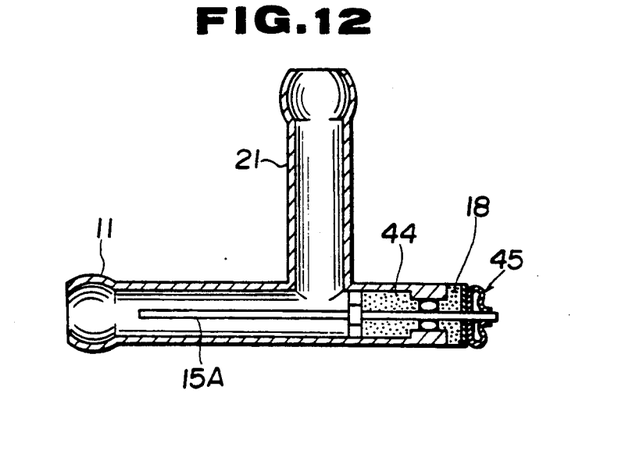
Figure 13:
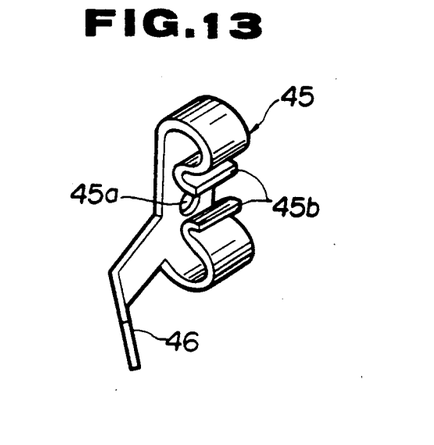
FIG. 13 is a perspective view of a spring retainer of the sensor system of FIG. 12.

FIG. 12 shows the fourth preferred embodiment of a sensor system, according to the present invention. In this embodiment, a spring retainer is substituted for the nut 19 of the first preferred embodiment in order to secure an internal electrode 15A to the cylindrical container 11. One end portion of the internal electrode 15A passing through a plug-type support member 44 to project from the cylindrical container 11, passes through an through opening 45a of the spring retainer 45 as shown in FIG. 13, and the tip of the internal electrode 15A is clamped by a pair of claws 45b. In this case, a member for preventing rotation of the internal electrode when fastening the nut, is not required. In addition, the spring retainer 45 is integrally formed with an output terminal 46, so that electrical connection is assured.

Figure 14:
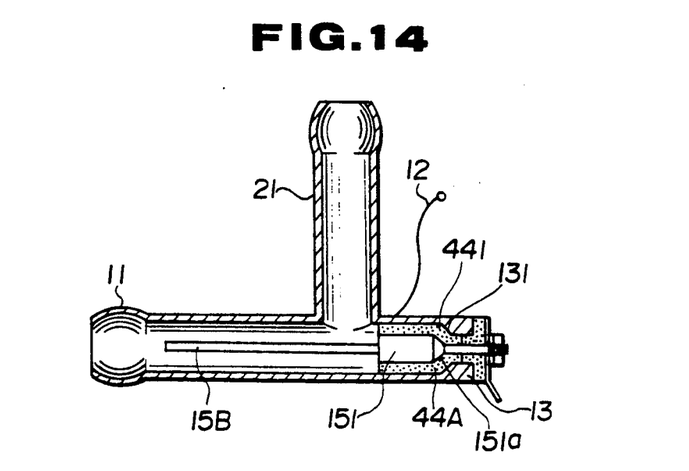
FIG. 14 is a sectional view of the fifth preferred embodiment of a sensor system according to the present invention.

FIG. 14 shows the fifth preferred embodiment of a sensor system, according to the present invention. In this embodiment, no O-ring is used for preventing leakage of fuel. The small-diameter portion 13 of the cylindrical container 11 is formed with a tapered surface 131 at its step. This tapered surface 131 comes into contact with a tapered surface 441 of a plug-type support member 44A, so as to interrupt leakage of fuel between the supporting member 44A and internal electrode 15B. In addition, the internal electrode 15B is formed with an essentially cylindrical large-diameter portion 151 at substantially a middle portion thereof. The large-diameter portion 151 has a tapered surface 151a on the side of the closed end portion of the cylindrical container 11. On the other hand, the plug-type support member 44A has a recessed portion for engaging the large-diameter portion 151 of the electrode. The recessed portion is formed with a tapered surface at the bottom thereof. This tapered surface comes into contact with the tapered surface 151a of the large-diameter portion 151 of the electrode so as to interrupt leakage of fuel between the internal electrode 15B and the support member 44A. In other words, the large diameter portion 151 and the tapered portion of the supporting member 44A collectively act as sealing means.

As mentioned above, according to the present invention, the sealing member arranged between the plug-type support member and the cylindrical container is designed to come into contact with the inner peripheral surface of the small-diameter portion of the cylindrical container. Since the inner peripheral surface of this small diameter portion can be more easily processed with high precision than the facing surface of the small diameter portion, sealing performance of the sealing member can be improved, according to the present invention.

In the shown embodiments, the invention is applied to a sensor system for detecting concentration or mixing ratio of mixed fuel. However, the invention can be applied to other sensor systems for measuring physical quantities which cause variation of the dielectric constant of fluids, rather than concentration.

While the present invention has been disclosed in terms of the preferred embodiment in order to facilitate better understanding thereof, it should be appreciated that the invention can be embodied in various ways without departing from the principle of the invention. Therefore, the invention should be understood to include all possible embodiments and modification to the shown embodiments which can be embodied without departing from the principle of the invention as set forth in the appended claims.

What is claimed is:

1. A sensor system for detecting a physical quantity of fluid, comprising:

a container serving as an external electrode and having a cylindrical inner wall means for defining a first cylindrical bore, said container having an annular inwardly projecting portion defining both a second cylindrical bore that is smaller in diameter than said first cylindrical bore and a shoulder at which said second cylindrical bore connects with said first cylindrical bore;

an internal electrode disposed within said cylindrical container;

a supporting member received within said container to hold said internal electrode at a predetermined position within said container;

a discharge pipe connected to said container and having one end opening to said first cylindrical bore at a predetermined portion and an opposite discharge end;

said supporting member having a cylindrical outer peripheral wall, first and second walls mutually spaced but interconnected by said cylindrical outer peripheral wall extending continuously therebetween, said first wall of said support member being disposed adjacent said predetermined portion and communicating with said one end of said discharge pipe, said second wall of said supporting member being in engagement with said shoulder defined by said inwardly projecting portion; and said second wall and said shoulder being constructed and arranged such that, when said supporting member is urged toward said shoulder upon being subject to a force, said second wall of said supporting member firmly engages said shoulder and a fluid flow from said first cylindrical bore toward said second cylindrical bore is restrained.

2. A sensor system as set forth in claim 1, wherein said supporting member has a through opening which extends in a direction of the longitudinal axis of the container and which receives therein a portion of the internal electrode so as to allow the internal electrode to extend in an essentially longitudinal direction of the container at the center thereof.

3. A sensor system as set forth in claim 2, wherein one end portion of said internal electrode passes through said through opening of the supporting member to project outside of the container.

4. A sensor system as set forth in claim 3, wherein said one end portion of the internal electrode is formed with a screw portion, and is fixed to the container by engaging the screw portion with a nut.

5. A sensor system as set forth in claim 3, wherein the end portion of said internal electrode extending in the longitudinal direction of the container has a rounded form so as to prevent agitation of the detected fluid passing through said container, and to decrease occurrence of bubbles in the detected fluid.

6. A sensor system as set forth in claim 2, wherein said internal electrode has a square pillar portion at substantially a central portion thereof, and said supporting member has a groove which engages the square pillar portion to prevent the internal electrode from rotating.

7. A sensor system as set forth in claim 4, wherein a hexagonal pillar portion is integrally formed with said internal electrode at a location neighboring the extended end portion of the internal electrode, to apply a whirl-stop to the internal electrode when fastening said nut.

8. A sensor system as set forth in claim 2, wherein said through opening of the supporting member comes tightly into contact with said internal electrode to prevent leakage of the detected fluid between the supporting member and the internal electrode.

9. A sensor system as set forth in claim 3, wherein said one end portion of the internal electrode engages a spring retainer to be fixed to the container.

10. A sensor system as set forth in claim 1, which further comprises a bush member which serves to thrust said sealing means against said supporting member.

11. A sensor system as set forth in claim 1, further comprising an O-ring disposed in said second cylindrical bore and positioned between said inwardly projecting portion and said internal electrode.

12. A sensor system as set forth in claim 1, wherein said supporting member is made of an electrical insulating material.

13. A sensor system as set forth in claim 1, wherein said sensor system forms a condenser between the external and internal electrodes to detect variation of electrostatic capacity of the condenser to obtain a dielectric constant of the detected fluid.

14. A sensor system as set forth in claim 1, wherein said discharge passage is connected to said container by way of brazing.

15. A sensor system as set forth in claim 1, wherein said second wall and said shoulder are conical and tapered.

16. A sensor system as set forth in claim 1, wherein said inwardly projecting portion has cylindrical wall means defining said second cylindrical bore.

17. A sensor system as set forth in claim 16, wherein said internal electrode extends through said supporting member into said second cylindrical bore.

18. A sensor system as set forth in claim 17, wherein said second wall of said supporting member has a surface portion extending inwardly beyond said shoulder defined by said inwardly projecting portion.

19. A sensor system as set forth in claim 18, further comprising a ring seal disposed in said second cylindrical bore.

20. A sensor system for detecting a physical quantity of fluid, comprising:

a container serving as an external electrode and having a cylindrical inner wall means for defining a first cylindrical bore, said container having an annular inwardly projecting portion defining both a second cylindrical bore that is smaller in diameter than said first cylindrical bore and a shoulder at which said second cylindrical bore connects with said first cylindrical bore;

an internal electrode disposed within said cylindrical container;

a supporting member received within said container to hold said internal electrode at a predetermined position within said container;

a discharge pipe connected to said container and having one end opening to said first cylindrical bore at a predetermined portion and an opposite discharge end;

said supporting member having a cylindrical outer peripheral wall, first and second walls mutually spaced but interconnected by said cylindrical outer peripheral wall, said first wall of said support member being disposed adjacent said predetermined portion and communicating with said one end of said discharge pipe, said second wall of said supporting member being in engagement with said shoulder defined by said inwardly projecting portion; and said second wall and said shoulder being constructed and arranged such that, when said supporting member is urged toward said shoulder upon being subject to a force, said second wall of said supporting member firmly engages said shoulder and a fluid flow from said first cylindrical bore toward said second cylindrical bore is restrained, and further comprising an O-ring disposed in said second cylindrical bore.

21. A sensor system for detecting a physical quantity of fluid, comprising:

a container serving as an external electrode and having a cylindrical inner wall means for defining a first cylindrical bore, said container having an annular inwardly projecting portion defining both a second cylindrical bore that is smaller in diameter than said first cylindrical bore and a shoulder at which said second cylindrical bore connects with said first cylindrical bore;

an internal electrode disposed within said cylindrical container;

a supporting member received within said container to hold said internal electrode at a predetermined position within said container;

a discharge pipe connected to said container and having one end opening to said first cylindrical bore at a predetermined portion and an opposite discharge end;

said supporting member having a cylindrical outer peripheral wall, first and second walls mutually spaced but interconnected by said cylindrical outer peripheral wall, said first wall of said support member being disposed adjacent said predetermined portion and communicating with said one end of said discharge pipe, said second wall of said supporting member being in engagement with said shoulder defined by said inwardly projecting portion; and said second wall and said shoulder being constructed and arranged such that, when said supporting member is urged toward said shoulder upon being subject to a force, said second wall of said supporting member firmly engages said shoulder and a fluid flow from said first cylindrical bore toward said second cylindrical bore is restrained, wherein said second wall and said shoulder are conical.

* * * * *